United States Patent [19]
Burstein et al.

[11] Patent Number: 5,698,410
[45] Date of Patent: Dec. 16, 1997

[54] HIGHLY SENSITIVE IMMUNOCYTOCHEMICAL METHOD FOR DIAGNOSIS OF MALIGNANT EFFUSIONS

[75] Inventors: David E. Burstein; Richard S. Haber, both of New York, N.Y.

[73] Assignee: Mount Sinai School of Medicine of the City University of New York, New York, N.Y.

[21] Appl. No.: 473,434

[22] Filed: Jun. 7, 1995

[51] Int. Cl.$^6$ .......................... G01N 33/574; G01N 33/53
[52] U.S. Cl. ..................... 435/7.23; 435/7.2; 436/63; 436/64; 436/813
[58] Field of Search ........................... 435/7.2, 7.23; 436/64, 813, 63

[56] References Cited

PUBLICATIONS

R. S. Brown, et al., "Intratumoral Distribution of Tritiated–FDG in Breast Carcinoma: Correlation between Glut–1 Expression and FDG Uptake," *The Journal of Nuclear Medicine*, 37(6):1042–1047 (Jun. 1996).

D. Kornrumpf, et al., "Overexpression of Glut–1 Glucose Transporter in Human Pancreatic Cancer—An Immunohistochemical Study," *The Journal of Nuclear Medicine*, 36(5):211P Proceedings of the 42 Annual Meeting (May 1995), Abstract.

S. Nagamatsu, et al., "Expression of Facilitative Glucose Transporter Isoforms in Human Brain Tumors," *Journal of Neurochemistry*, 61(6):2048–2053 (Dec. 1993).

T. Higashi, et al., "Overexpression of GLUT–1 Glucose Transporter in Human Malignant Pancreatic Tumors Immunohistochemical Study of Glucose–1,2,3,4 and 5 Glucose Transporters," *Gastroenterology*, 110(4):A528 (Apr. 1996), Abstract.

M. Younes, et al., "Glucose Transporter Glut 1 is Frequently Expressed in Colon Cancer," U.S. Canadian Acad. Pathology 1995 Meeting, Mar. 11–19, p. 71A, Abstract No. 404 (1995).

Abati, et al., *Diagnostic Cytopathology*, vol. 11, No. 1, 64–67, 1994 (Abstract only).

Woods, et al., *Lancet* 2 (8297) 512–514, 1982 (Abstract only).

Danner, et al., *Acta Cytology*, vol. 19, No. 6, 509–518, 1975 (Abstract only).

Y. Noguchi, et al., "Expression of Glucose Transporters and Insulin Resistance in Human GI Cancer," *Proceedings of the American Association for Cancer Research*, 36:205 (Mar. 1995).

M. Younes, et al., "Most Non–Small Cell Lung Cancers (LCA) Express the Human Erythrocyte Glucose," *Proceedings of the American Association for Cancer Research*, 36:249 (Mar. 1995).

G. Boden, et al., "Glucose Transporter Proteins in Human Insulinoma," *Annals. of Internal Medicine*, 121(2):109–112 (Jul. 1994).

R. S. Brown, and R. L. Wahl, "Overexpression of Glut–1 Glucose Transporter in Human Breast Cancer," *Cancer*, 72(10):2979–2985 (Nov. 1993).

P. Mellanen, et al., "Expression of Glucose Transporters in Head–and–Neck Tumors," *Int. J. Cancer*, 56:622–629 (1994).

Y. Nagase, et al., "Immunohistochemical Localization of Glucose Transporters in Human Renal Cell Carcinoma," *The Journal of Urology*, 153:798–801 (Mar. 1995).

T. Yamamoto, et al., "Over–Expression of Facilitative Glucose Transporter Genes in Human Cancer," *Biochemical and Biophysical Research Communications*, 170(1):223–230 (1990).

*Primary Examiner*—Toni R. Scheiner
*Attorney, Agent, or Firm*—Hamilton, Brook, Smith & Reynolds, P.C.

[57] ABSTRACT

Disclosed is a method of detecting malignancy in a body cavity effusion. Also disclosed is a method of distinguishing a benign hyperplastic lymph node from a lymph node involved by a low grade follicular lymphoma. Also disclosed is a method of distinguishing a benign tumor from a malignant tumor which overexpresses GLUT-1.

10 Claims, No Drawings

HIGHLY SENSITIVE IMMUNOCYTOCHEMICAL METHOD FOR DIAGNOSIS OF MALIGNANT EFFUSIONS

BACKGROUND OF THE INVENTION

Abnormal collections of fluids in a body cavity of an individual, referred to as effusions, are often caused by malignant tumors. An effusion can also be the first sign that a tumor which had been surgically removed or had undergone remission is metastasizing. However, an effusion can have many causes that are unrelated to cancer, e.g. heart failure, liver dysfunction and pneumonia. Presently, the standard method of determining whether an effusion is caused by a cancer from an effusion resulting from other causes is to remove some of the effusion fluid, isolate the cells contained therein, and examine the cells morphologically. However, this method of diagnosis leaves a significant percentage of cancers undetected. A more reliable method of determining whether an effusion is cancer-related would allow earlier intervention with treatment and can increase the likelihood of better clinical outcomes.

In many cases it is difficult to determine whether a tumor or nodule is malignant without surgically removing the suspected tissue. For example, when a thyroid nodule is detected, one method for distinguishing benign from malignant nodules is cytologic examination of cells obtained by fine needle aspiration (FNA). Routine cytologic examination of FNA specimens is, however, far from satisfactory. Even when adequate specimens are obtained the cytologic report is often indeterminate because of the inherent inability of routine cytology to distinguish benign from malignant follicular neoplasms (adenoma vs. carcinoma) when a microfollicular pattern is seen. This frequently leads to surgical excision of these nodules, the majority of which are ultimately found to be benign (Mazzaferri, E. L., *New Engl. J. Med.* 328:553–559, 1993). In addition, concern about false-negative reports when the cytologic diagnosis is benign may also lead to surgery. As a result, the majority of patients who have thyroid surgery for nodules turn out to have benign disease, even with the extensive use of FNA and routine cytology (Mazzaferri, E. L., *Am. J. Med.* 93:359–362, 1992; Cusick, et al., *Br. Med. J.* 301:318–321, 1990). Consequently, there is a need for a more accurate method of distinguishing between malignant and benign tumors prior to surgery.

SUMMARY OF THE INVENTION

The present invention is based on the discovery that cancer cells in body cavity effusions can be detected by immunostaining of the transmembrane glucose transporter protein GLUT-1 in malignant effusions. As discussed herein, GLUT-1 is overexpressed in many malignancies. Sites of origin of GLUT-1 positive malignant cells in effusions included ovary, lung, breast, biliary tract, endometrium, and carcinomas of unknown primary.

It has also been found unexpectedly that GLUT-1 is underexpressed in neoplastic follicles from low grade follicular lymphomas compared with benign hyperplastic lymph nodes. Consequently, these lymphatic malignancies can be identified by diminished immunostaining.

Another aspect of the present invention is a method of distinguishing between malignant and benign tumors based on assessment of expression of transmembrane GLUT-1 in cells from tissue samples. That is, overexpression of transmembrane GLUT-1 has been shown to aid in distinguishing between malignant and benign tumors; overexpression can be identified by immunostaining. Cancers which overexpress GLUT-1 include ovary, lung, breast, biliary tract, endometrium, squamous cell carcinoma of head and neck origin, leiomyosarcoma, kidney, thyroid, bladder, colon and carcinomas of unknown primary.

The present invention is a method of detecting malignancy in a body cavity effusion. A cytologic cell block preparation is prepared from a body cavity effusion, thereby obtaining a test preparation. The level of GLUT-1 expression (i.e., in the test preparation) is then assessed. The level of GLUT-1 expression in an appropriate control is compared with the level of GLUT-1 expression in cells from the cell block. The control is a cell block produced from a benign body cavity effusion; GLUT-1 expression in cells in the cell block is assessed and is the level of GLUT-1 expression to which the GLUT-1 level in the test preparation is compared (the effusion being assessed). A lower level of GLUT-1 expression in the control compared with the cells from the effusion being assessed is indicative of malignancy in the body cavity effusion being assessed.

Another embodiment of the present invention is a method of distinguishing a benign hyperplastic lymph node from a lymph node involved by a low grade follicular lymphoma. In this embodiment, a tissue sample is obtained from a section of a lymph node suspected of being involved by a low grade follicular lymphoma. The level of GLUT-1 expression in the cells from the tissue sample is assessed. The level of GLUT-1 expression in an appropriate control is compared with the level of GLUT-1 expression in the cells of the tissue sample being assessed. The control is the amount of GLUT-1 expressed in the cells from a benign hyperplastic lymph node. A lower level of GLUT-1 expression in the tissue sample being assessed, compared with the level in the control, indicates that the tissue sample being assessed is involved by a low grade follicular lymphoma.

Yet another embodiment of the present invention is a method of distinguishing a benign tumor from a malignant tumor which overexpresses GLUT-1. A tissue sample is obtained from a section of a tumor suspected of being malignant. GLUT-1 expression in cells from the tissue sample is assessed. The level of GLUT-1 expression in an appropriate control is compared with the level of GLUT-1 expression in the tissue sample being assessed. The control is the amount of GLUT-1 expressed in the cells from a tissue sample obtained from a section of a non-malignant tissue from the same tissue type as the tissue sample being assessed. A higher level of GLUT-1 expression in the sample being assessed compared with the control indicates that the tissue sample being assessed is involved by a malignant tumor.

Since immunocytochemistry is relatively inexpensive and routinely used in clinical pathology laboratories, GLUT-1 immunostaining has the potential for widespread clinical application.

DETAILED DESCRIPTION OF THE INVENTION

Many types of cancer cells have markedly increased glucose utilization, resulting from a predominantly glycolytic rather than oxidative utilization of glucose, even in the presence of oxygen (Warburg, O., *Science* 123:309–314, 1956). Because the metabolism of glucose to lactate yields only 2 moles of ATP/mole glucose, as opposed to 36 moles of ATP produced by oxidative metabolism, cancer cells are forced to increase their glucose utilization many-fold compared to normal cells. Since glucose transport across the plasma membrane is rate-limiting for glucose utilization in cancer cells and many normal cells as well, cancer cells have markedly increased glucose transport rates (Hatanaka, M., Biochem. Biophys. Acta. 355:77–104, 1974; Weber, M. et al., J. Cell Physiol. 89:711–721, 1976; Elbrink, J. and I. Bihler, Science 188:1177–1184, 1975). indeed, transformation of cultured cells is accompanied by a five- to ten-fold increase in glucose transport and in glucose transporter gene expression (Flier, J. S. et al., Science 235:1492–1495, 1987; Birnbaum, M. J. et al., Science 235:1495–1498, 1987).

The facilitated diffusion of glucose into cells is mediated by a family of five homologous proteins, GLUT-1–GLUT-5, which were cloned and identified from 1986–1989 (Pessin, J. E. and G. L. Bell, Annu. Rev. Physiol. 54:911–930, 1992). The glucose transporter isoforms differ in their tissue distribution and functional characteristics. The GLUT-1 isoform is the focus of the present application.

Although GLUT-1 is expressed in many organs, immunohistochemical studies demonstrate its expression mainly in erythrocytes (red blood cells) and in cells which constitute blood-tissue barriers. For example, in brain GLUT-1 is seen only in the capillary endothelium of the blood-brain barrier (Boado, R. J. and Wm. Pardridge, Biochem. Biophys. Res. Commun. 166:175, (1990)); in muscle it is found only in the perineurium of innervating nerves (blood-nerve barrier) (Froehner, S. C. et al., J. Neurocytol. 17:173–178, 1988)). In addition, in routinely prepared tissue sections of skin and squameous epithelia, GLUT-1 is found in basal cells by immunostaining. However, benign parenchymal cells of most tissues do not stain for GLUT-1 immunohistochemically, even with the sensitive avidin-biotin-peroxidase method.

Experimental evidence indicates that malignant cells over-express GLUT-1. Transformation of cultured cells with src and ras oncogenes or sarcoma virus promptly increases glucose transporter protein and GLUT-1 mRNA by 5–10 fold (Flier, J. S. et al., Science 235:1492–1495, 1987; Birnbaum, M. J. et al., Science 235:1495–1498, 1987). GLUT-1 mRNA in a variety of gastrointestinal cancers (Yamamoto, T. et al., Biochem. Biophys. Res. Commun. 170:223–230, 1990) and in hepatoma (Su, T-S. et al., Hepatology 11:118–122, 1990) is expressed at higher levels than in corresponding normal tissue. High levels of GLUT-1 mRNA (Northern blotting) and protein (immunohistochemistry) were also found in a series of head-and-neck squamous cell carcinomas (Mellanen, P. et al., Int. J. Cancer 56:622–629, 1994). An immunohistochemical study of GLUT-1 expression in breast cancer (using archival formalin-fixed paraffin sections) also found variably increased staining, whereas normal breast tissue stained only weakly or not at all (Brown R. S. and R. L. Wahl, Cancer 72:2979–85, 1993). The only other isoform which has been thought to be overexpressed in cancer is GLUT-3, based on reports of increased GLUT-3 mRNA without measurement of GLUT-3 protein (Yamamoto, T. et al., Biochem. Biophys. Res. Commun., 170:223–230, 1990; Mellanen, P. et at., Int. J. Cancer 56:622–629, 1994). However, Northern blotting for GLUT-3 mRNA has proved to be a false indicator of the presence of GLUT-3 protein in many tissues (Haber, R. S. et al., Endocrinology 132:2538–2543, 1993), and we have not detected GLUT-3 protein in immunoblots from a wide variety of human cancers.

The present invention is a method of diagnosing cancers. A "method of diagnosing cancer" can be used to distinguish between malignant and benign tissue, for example determining whether a tumor or nodule is benign or malignant. It can also be used to determine the presence or absence of cancer in an individual. For example, an effusion, which can have many other causes, is often the first sign that a cancer exists or that a tumor which had been surgically removed or gone into remission has metastasized. The methods of the present invention can determine whether an effusion is due to a cancer whose primary site may be known or unknown or is due to other causes. Alternatively, the methods of the present invention can be used as an aid in diagnosing cancer. An "aid in diagnosing cancer" is used in conjunction with other medical tests to determine the presence or absence of cancer in an individual or determine whether particular tissue is malignant or benign.

An effusion is an abnormal collection of fluid in a body cavity. The present method is applicable to effusions from body cavities, such as the abdominal cavity (the peritoneal cavity), the pleural cavities (the spaces that line lung) and the pericardium cavity (the spaces that line the heart). Methods of obtaining an effusion are well known in the art and typically involve puncturing the chest wall or abdominal wall with a needle and evacuating the fluid.

A cytological cell block is a preparation of biological material from an effusion. Typically, a cytological cell block is obtained by providing a sample of an effusion and concentrating the cells contained therein. Cells are concentrated from an effusion by, for example, centrifugation. After concentration, the cells are typically fixed in formalin or alcohol and imbedded in paraffin as is routinely done for surgical pathology.

As used herein, a "tissue sample" is a collection of cells taken from tissue and is used to obtain a determination of GLUT-1 expression that is sufficiently precise to distinguish malignant cells which overexpress GLUT-1 from non-malignant cells. Methods of obtaining tissue samples are well known in the art and include samples from surgically excised tissue. Tissue samples and cellular samples can also be obtained without the need for invasive surgery, for example by puncturing the chest wall or the abdominal wall or from masses of breast, thyroid or other sites with a fine needle and withdrawing cellular material (fine needle aspiration biopsy). The tissue samples can then be fixed in formalin or alcohol and imbedded in paraffin as is routinely done for surgical pathology. Alternatively, the cells can be applied directly from the fine needle to a microscope slide.

An appropriate control is the level of GLUT-1 expression in cells taken from a benign body cavity effusion or a sample taken from benign tissue of the same type that is being assessed. The level of GLUT-1 expression be determined prior to, simultaneously with, or subsequent to the determination of the level of GLUT-1 expression in the tissue or effusion being assessed. In practice benign effusions and benign tumors show nonexistent to weak staining of cells; malignant effusions and tumors show intense staining of the membranes of malignant cells. In practice benign follicles show positive staining whereas malignant follicles are non-staining for GLUT-1. Because the staining properties of benign and malignant cells differ so dramatically, the control is normally not performed at the same time that the tissue sample or effusion is being assessed and in many cases is not needed.

The levels of GLUT-1 expression from tissue samples or cytological cell blocks can be determined by immunostaining. The primary antibody is a well-characterized rabbit antiserum raised against a 13-amino acid peptide corresponding to the C-terminal of GLUT-1 (Hasper, H. C. et al., J. Biol. Chem. 263:398–403, 1988), obtained commercially (East Acres Biologicals). This antibody recognizes both rat and human GLUT-1 which share the peptide sequence, but does not crossreact with other GLUT isoforms, which are highly divergent at the C-terminus. Analogously obtained polyclonal or monoclonal antibodies can also be used. Bound antibody is detected by a routine avidin-biotin-peroxidase method (Vectastain kit, VECTOR). To demonstrate the specificity of staining, antiserum pre-incubated with the immunizing peptide (20 µg/ml) is used to stain parallel tissue sections.

The antiserum gave strong specific (peptide-compatible) staining of GLUT-1 in capillary endothelium in brain (blood-brain barrier), in erythrocytes, in basal cells of benign squameous epithelia, and in perineurium of peripheral nerve, all of which are sites of high GLUT-1 expression. In contrast, parenchymal cells of a wide variety of normal tissues were negative for GLUT-1. An antibody dilution of 1:500 was found to be optimal.

Immunohistochemical GLUT-1 staining has been performed with formalin-fixed tissue sections from a wide variety of cancers, including carcinomas of lung, breast, colon, ovary, endometrium, stomach, and kidney, squamous cell carcinoma, lymphoma, bladder carcinoma, and seminoma. In preliminary studies, 70% of the cases examined (17 out of 24) showed specific GLUT-1 staining in tumor cells. This staining was typically variable within each tumor, with discrete foci of positivity. In no case was specific GLUT-1 staining seen in adjacent normal parenchymal cells. Moreover, those tumors with the highest concentrations of GLUT-1 by immunoblot analysis had the most intense GLUT-1 staining in the tumor cells.

GLUT-1 expression in cell blocks prepared for routine cytology from benign and malignant pleural and peritoneal effusions has also been studied. Immunostaining methodologies were applied to the detection of GLUT-1 in cytologic preparations of body cavity effusions. Using standard avidin-biotin immunostaining, cell blocks were examined from 76 body cavity effusions or washings. Of 58 technically appropriate cell block preparations, GLUT-1 staining occurred in 30 out of 32 malignant effusions. Sites of origin included ovary, lung, breast, biliary tract, endometrium, and carcinomas of unknown primary. The only mesothelioma tested stained positively for GLUT-1. Characteristic staining pattern consisted of dense, linear staining of the plasma membrane, with accentuation at cell—cell borders, with or without cytoplasmic staining. Specificity of GLUT-1 staining was further defined by competability by preincubation of antiserum with the immunizing 13 amino acid peptide from the carboxyl terminal of GLUT-1. Red blood cells showed similar membrane staining, consistent with previous reports. Of 26 benign effusions, 21 were nonstaining, and 5 showed rare mesothelial cells with equivocal to very weak membrane staining which was readily distinguishable from the characteristic strong staining of malignant cells and easily distinguished by benign morphological characteristics; at least 3 of these 5 cases were from patients with cirrhosis. In all other cases, mesothelial cells, histiocytes and other inflammatory cells were nonstaining.

These findings show that GLUT-1 immunostaining alone or in a panel of markers, for example immunohistochemical or histochemical markers, can be used in diagnostic cytopathology.

In addition to being useful to distinguish benign from malignant thyroid disease, GLUT-1 immunostaining may also prove useful as a prognostic indicator in certain kinds of cancer, for example thyroid cancer. Since the increase in glucose utilization in other tumors correlates with clinical aggressiveness (DiChiro, G. et al., *Neurology* 32:1323–1329, 1982), it is likely that cancers with the greatest malignant potential will have the greatest overexpression of GLUT-1. Intense GLUT-1 immunostaining might thus be a marker for those cancers with the poorest prognosis. This could be used to help select patients for more aggressive treatment and surveillance.

As discussed above, many cancers over-express GLUT-1. Quite unexpectedly, it has been found that GLUT-1 is underexpressed in neoplastic follicles from low grade follicular lymphomas. Tissue samples taken from lymph nodes showing neoplastic lymph follicles were observed to exhibit less immunostaining than normal follicle-like "germinal centers". This observation can be used as the basis for a method of diagnosing and as an aid in diagnosing low grade follicular lymphomas. These tumors can be distinguished from normal tissue by assessing GLUT-1 expression in the follicles of the lymph node. Less GLUT-1 expression in the tissue sample than in an appropriate control, e.g. the level of expression typically observed in non-malignant lymphoid follicles, or the absence of GLUT-1 expression in follicles is indicative of a low grade follicular lymphoma. GLUT-1 expression can be determined, for example, by immunostaining, as described above. Low grade follicular lymphomas show less follicular staining than normal follicles in lymph node biopsies.

The invention is illustrated by the following examples, which are not to be construed as limiting in any way.

EXAMPLE 1

Distinguishing Malignant Thyroid Nodules From Benign Thyroid Nodules Using Immunocytochemical Staining for GLUT-1 Glucose Transporter Preparation of crude membranes from thyroid tissue for immunoblot analysis. A fragment of thyroid tissue (ca. 0.5 g) was obtained from fresh surgical tissue and stored at −80° C. Crude membranes were prepared as previously described (Haber, R. S. et al., *Endocrinology* 132:2528–2543, 1993). The tissue was homogenized (Polytron), nuclei and unbroken cells were sedimented and discarded, and a total membrane fraction was prepared by ultracentrifugation. Protein concentration was determined by the Lowry method.

Preparation of cytologic "touch prep" slides and frozen histologic sections from thyroid tissue. Glass slides were coated with aminoalkylsilane to promote cell adhesion. The slides were dabbed against a cut surface of a freshly-excised tumor, and immediately sprayed with ethanolic cytology fixative. Routine frozen sections were fixed in ethanol.

Fine needle aspirates of thyroid tissue. Freshly-excised surgical thyroid tissue were subjected to fine needle aspiration using a 22-gauge needle, 10-cc syringe, and Cameco syringe pistol. Aspirates were smeared between two glass slides and immediately sprayed with cytology fixative as for routine clinical FNA. This procedure is meant to mimic standard clinical FNA as closely as possible.

GLUT-1 immunostaining. GLUT-1 protein in cytologic preparations was detected by standard avidin-biotin-peroxidase immunocytochemistry. Cellular specimens on glass slides are rehydrated through graded ethanol, washed in phosphate-buffered saline (PBS), and blocked with 5% goat serum in PBS. They were then incubated with rabbit anti-GLUT-1 serum at 1:500 dilution (with or without preincubation of the antiserum with the immunizing peptide at 20 µg/ml to confirm signal specificity). Both GLUT-1 antiserum and GLUT-1 peptide are commercially available from East Acres Biologicals (Southbridge, Mass.). The slides were then washed and incubated with secondary antibody (biotinylated goat and anti-rabbit 1:200). After blocking of endogenous peroxidase with 0.3% $H_2O_2$, bound antibody was detected with avidin-biotin-peroxidase complex (Vectastain kit, Vector Labs) using diaminobenzidene as a chromogen. The slides were counter-stained with hematoxylin, dehydrated in graded ethanol and xylene, and mounted with coverslips. Microscopic interpretation. Immunostained specimens were graded for specific GLUT-1 staining without prior knowledge regarding the source of the specimen. The criteria for specific staining were inhibition of the signal by competition with the immunizing GLUT-1 peptide. Cellular GLUT-1 is known to be distributed between the plasma membrane and intracellular vesicles (Yang, J. et al., *J. Biol. Chem.* 267:10393–10399, 1992). The subcellular pattern of staining (peripheral vs. intracellular) and the intensity of staining (1+ to 4+) was also noted.

For correlation of GLUT-1 immunostaining results with routine cytologic diagnosis in thyroid, parallel slides were stained (Papanicolauou) and examined microscopically by the same blinded observer. Aspirates were assigned cytologic diagnosis of: a) benign, b) malignant or suspicious for malignancy, c) indeterminate, or d) inadequate specimen.

To confirm specificity parallel tissue sections were stained using antiserum that had been pre-incubated with the immunizing peptide. There were 31 benign cases (19 follicular adenoma, 1 Hurthle cell adenoma, 6 nodular goiter, 3 lymphocytic thyroiditis, 2 Graves' disease) and 23 cases of thyroid cancer (9 papillary, 4 follicular variant of papillary, 5 follicular, 1 Hurthle cell, 2 anaplastic, 2 medullary). Normal thyroid tissue adjacent to nodules showed no thyrocyte staining in any case. As expected, there was strong specific GLUT1 staining in erythrocyte membranes and in perineurium. No GLUT1 staining was seen in thyrocytes in benign nodular tissue, except for a single case of thyroiditis in which some foci of Hurthle cells showed weak staining. Among the thyroid cancers, 9/23 (39%) showed GLUT1 staining in tumor cells. This included 9/13 cases of papillary carcinoma and its follicular variant, 1/5 cases of follicular carcinoma and 2/2 cases of anaplastic carcinoma. Tumor cell GLUT1 staining was seen in two patterns: focal circumferential plasma membrane staining at the center of tumor cell nests, or asymmetric staining of the basilar aspect of tumor cells adjacent to stroma in some cases of papillary carcinoma. We conclude that GLUT1 protein is frequently overexpressed in thyroid cancer. GLUT1 immunostaining may be potentially useful in the cytologic diagnosis of thyroid nodules.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting malignancy in a body cavity effusion, comprising the steps of:
   (a) preparing a cytologic cell block preparation from a body cavity effusion, thereby obtaining a test preparation;
   (b) assessing the level of GLUT-1 expression in the cells from the cell block;
   (c) comparing the level of GLUT-1 expression in an appropriate control, wherein the control is the level of GLUT-1 expression in the cells from a cell block obtained from a benign body cavity effusion,
   wherein a higher level of GLUT-1 expression in (b) compared with the control is indicative of malignancy in the body cavity effusion.

2. The method of claim 1 wherein the level of GLUT-1 expression in cells from the cell block is assessed by the steps of:
   (a) contacting the test preparation with an antibody which binds transmembrane glucose transporter GLUT-1, under conditions appropriate for the antibody to bind transmembrane glucose transporter GLUT-1;
   (b) assessing binding of the antibody and transmembrane glucose transporter GLUT-1 in the test preparation.

3. The method of claim 2 wherein the binding of antibody is assessed by the intensity of cell membrane staining, wherein intense staining is indicative of malignancy in the body cavity effusion.

4. The method of claim 1 wherein the level of GLUT-1 expression in cells from the cell block is assessed by the steps of:
   (a) contacting the test preparation with an antibody which binds transmembrane glucose transporter GLUT-1, under conditions appropriate for the antibody to bind transmembrane glucose transporter GLUT-1, whereby if GLUT-1 is present in the text preparation, GLUT-1/antibody complexes are formed; and
   (b) incubating complexes formed in (a) with an agent which binds the complex, under conditions appropriate for binding of the agent and the complex to occur; and
   (c) assessing the extent of binding in (b).

5. A method of distinguishing a benign body cavity effusion from a malignant body cavity effusion, comprising the steps of:
   (a) preparing a cytologic cell block preparation from a body cavity effusion, thereby obtaining a test preparation;
   (b) contacting the test preparation with an antibody which binds transmembrane glucose transporter GLUT-1, under conditions appropriate for the antibody to bind transmembrane glucose transporter GLUT-1;
   (c) determining binding of the antibody and GLUT-1; and
   (d) comparing the binding determined in (c) with binding of the antibody with a control preparation, wherein the control preparation is a cytologic cell block prepared from a benign body cavity effusion,
   wherein the body cavity effusion is a malignant body cavity effusion if the antibody binds the test preparation to a greater extent than the antibody binds the control preparation and the body cavity effusion is a benign body cavity effusion if the antibody binds the test preparation and the control preparation to a similar extent.

6. A method of distinguishing a benign hyperplastic lymph node from a lymph node involved by a low grade follicular lymphoma, comprising the steps of:
   (a) obtaining a tissue sample from a section of a lymph node suspected of being involved by a low grade follicular lymphoma;
   (b) assessing the level of GLUT-1 expression in the follicles from the tissue sample;
   (c) comparing the level of GLUT-1 expression in the follicles from the tissue sample with an appropriate control, wherein the control is the level of GLUT-1 expression in the follicles from a tissue sample obtained from a section of a benign hyperplastic lymph node,
   wherein a lower level of GLUT-1 in b) compared with the control indicates that the tissue sample of a) is involved by a low grade follicular lymphoma.

7. The method of claim 6 wherein the level of GLUT-1 expression in the follicles from a tissue sample is determined by the following steps:

(a) contacting the tissue sample with an antibody which binds GLUT-1 under conditions appropriate for the antibody to react with GLUT-1;

(b) incubating the complex of a) with an agent that will bind the complex under conditions appropriate for binding to occur; and (c) detecting the extent of binding occurring in b).

8. A method of distinguishing a benign tumor from a malignant tumor, wherein the malignant tumor is suspected of being from a type of cancer which overexpresses GLUT-1, comprising the steps of:

(a) obtaining a tissue sample from a section of a tumor suspected of being malignant;

(b) assessing the level of GLUT-1 expression in the cells from the tissue sample;

(c) comparing the level of GLUT-1 expression in an appropriate control, wherein the control is the amount of GLUT-1 expression in the cells from a tissue sample obtained from a section of a non-malignant tissue from the same tissue type taken in step (a), wherein a higher level of GLUT-1 expression in b) compared with the control indicates that the tissue sample of a) is involved by a malignant tumor.

9. The method of claim 8 wherein the level of GLUT-1 expression in the of cells from a tissue sample is determined by the following steps:

(a) contacting the tissue sample with an antibody which binds GLUT-1 under conditions appropriate for the antibody to react with GLUT-1;

(b) incubating the complex of a) with an agent that will bind the complex under conditions appropriate for binding to occur;

(c) detecting the extent of binding occurring in b).

10. The method of claim 9 wherein the extent of binding between the agent and the complex is determined by the intensity of cell membrane staining, wherein intense staining is indicative that the tissue sample is involved by a malignant tumor.

* * * * *

UNITED STATES PATENT AND TRADEMARK OFFICE
CERTIFICATE OF CORRECTION

PATENT NO. : 5,698,410

DATED : December 16, 1997

INVENTOR(S) : David E. Burstein and Richard S. Haber

It is certified that error appears in the above-identified patent and that said Letters Patent is hereby corrected as shown below:

Column 10, line 7, after the words "expression in the", delete the word ---of---.

Signed and Sealed this

Seventh Day of April, 1998

*Attest:*

BRUCE LEHMAN

*Attesting Officer*  Commissioner of Patents and Trademarks